United States Patent [19]
Knight

[11] Patent Number: 5,675,063
[45] Date of Patent: Oct. 7, 1997

[54] IMMORTALIZED RABBIT HYBRIDOMA FUSION PARTNER

[75] Inventor: Katherine L. Knight, Chicago, Ill.

[73] Assignee: Loyola University of Chicago, Maywood, Ill.

[21] Appl. No.: 396,383

[22] Filed: Feb. 28, 1995

[51] Int. Cl.⁶ .............................. C12N 15/00; C12N 5/12; C12N 15/06; C12N 5/24
[52] U.S. Cl. .................. 800/2; 435/172.3; 435/240.26; 435/240.27; 935/70; 935/89; 935/93; 935/106
[58] Field of Search ................. 435/172.2, 172.3, 435/240.2, 240.26, 240.27; 800/2, DIG. 1, DIG. 6; 935/70, 89, 93, 95, 102

[56] References Cited

U.S. PATENT DOCUMENTS

| | | | |
|---|---|---|---|
| 4,736,866 | 4/1988 | Leder et al. | 800/2 |
| 4,859,595 | 8/1989 | Strosberg et al. | 435/172.2 |
| 5,073,490 | 12/1991 | Babinet et al. | 435/240.2 |

FOREIGN PATENT DOCUMENTS 0 200 231  2/1986  European Pat. Off. .

OTHER PUBLICATIONS

Shamay et al., Transf. Res. 1: 124–132 (1992).
Life Technologies 1993–1994 Catalog, pp. 21–23 and 21–24.
Adams et al., *Nature*, 318, 533–538 (1985).
Adams et al., *Science*, 254, 1161–1167 (1991).
Kappel et al., *Current Opinion in Biotechnology*, 3, 548–553 (1992).
Knight et al., *Proc. Natl. Acad. Sci.*, 85, 3130–3134 (1988).
Rosenbaum et al., *The EMBO Journal*, 9, 897–905 (1990).
Sethupathi et al., *Leukemia*, 8, 2144–2155 (1994).
Stewart et al., *Cell*, 38, 627–637 (1984).
World Patents Index, Derwent Publications Ltd., AN 87-280948/40 (1987) (JP 62195296 abstract).

*Primary Examiner*—Jasemine C. Chambers
*Assistant Examiner*—Karen M. Hauda
*Attorney, Agent, or Firm*—Leydig, Voit & Mayer, Ltd.

[57] ABSTRACT

Novel methods are provided for producing rabbit fusion partners for the production of specific binding proteins, particularly immunoglobulins. Nuclei of rabbit fertilized ova are microinjected with an oncogene to express specifically in lymphoid cells (i.e., lymphoid specific) and the embryos are then implanted in appropriate hosts. The newborns are maintained to sexual maturity and are either mated with rabbit hosts that developed from embryos that had been microinjected with a different lymphoid-specific oncogene or their fertilized eggs are microinjected with another oncogene specific for lymphoid cells. The immortalized lymphoid cells that develop in these animals may be genetically altered and used as fusion partners to produce rabbit hybridomas for the production of monoclonal antibodies.

25 Claims, No Drawings

IMMORTALIZED RABBIT HYBRIDOMA FUSION PARTNER

STATEMENT AS TO RIGHTS TO THE INVENTION MADE UNDER FEDERALLY-SPONSORED RESEARCH AND DEVELOPMENT

This invention was made with U.S. Government support (Public Health Service Grant AI 11234). The Government may have certain rights in this invention.

BACKGROUND OF THE INVENTION

Monoclonal antibodies are widely used in research and in the diagnosis and treatment of numerous diseases. Typically, monoclonal antibodies are produced in mice, rats or hamsters because (1) several hybridoma fusion partners have been derived from these species, and/or (2) stable heterohybridomas can be obtained by fusions between cells of various rodent species. There is, however, a critical need for hybridomas from other species that can recognize antigens and epitopes that are not recognized by mice, rat or hamster-derived reagents. Accordingly, it is an object of this invention to generate an immortalized plasmacytoma cell line, from a species such as rabbit, that can be used as a hybridoma fusion partner for generating monoclonal antibodies.

The availability of rabbit monoclonal antibodies (MAb), for example, is valuable for many reasons. First, rabbits are known to produce antibodies to many antigens that are not especially immunogenic in mice. Direct comparisons of rabbit and mouse antibodies directed against human melanoma cells have shown that rabbit and mouse antibodies recognize different epitopes. Second, rabbit antibodies are generally of higher affinity than mouse antibodies. Third, because most MAb are generated in mouse and rat, there are relatively few MAb that react with mouse or rat immunogens. This is because they do not make anti-self antibodies and because rat and mouse are phylogenetically so close that their antigens are highly similar.

Until now, a fusion partner from which rabbit MAb could be generated had not been developed because rabbit plasmacytomas were not available. Several laboratories developed mouse-rabbit heterohybridomas, but this technology has had only limited success. The earliest mouse-rabbit heterohybridomas were unstable and/or secreted only light chain fragments. Although subsequent investigators attempted to overcome this problem by using normal rabbit serum (NRS) instead of fetal calf serum (FCS) as a supplement to the culture medium, the methodology remains flawed. Because the heterohybridomas are highly unstable, they need to be subcloned every four to six weeks in order to avoid loss of antibody secretion. In our laboratory, we obtained no more than two to five heterohybridomas per fusion. In addition, such heterohybridomas are difficult to clone, and the clones are generally unstable and do not secrete antibody over a prolonged period of time.

It would be desirable to have same species hybridomas where both the fusion partner and the cells to be fused are derived from the same species, for example, rabbit-rabbit. Such same-species hybridomas would be more stable than heterohybridomas and thereby produce long-lasting cell lines that would continue to secrete antibody over a prolonged period of time. This is because the same-species hybridomas are much less likely than heterohybridomas to delete chromosomes. Such same-species hybridomas will be useful not only for generating monoclonal antibodies but also for studying immunoglobulin genes, including the mechanism of V, (D), J gene rearrangements, allelic exclusion and somatic diversification.

SUMMARY OF THE INVENTION

The present invention relates to a fusion partner from which stable same-species hybridomas can be developed. In one method, double transgenic rabbits that developed lymphoid cells suitable for use as a fusion partner were produced; the fusion partners were then used to make rabbit-rabbit hybridomas.

The invention further relates to producing fusion partners for the production of specific binding proteins, preferably immunoglobulins. A method according to the invention involves using certain cells, e.g., plasmacytomas from transgenic rabbits, as fusion partners to produce same-species hybridomas capable of producing monoclonal antibodies.

Finally, the invention relates to transgenic rabbits carrying at least two transgenes, c-myc and v-abl. The transgenic offspring developed plasmacytomas that could be cultured and used as a fusion partner. This fusion partner was used to produce stable rabbit-rabbit hybridomas that secreted antibodies specific for the immunogen.

DETAILED DESCRIPTION OF THE INVENTION

More particularly, the invention includes an immortalized cell line referred to herein as a hybridoma fusion partner. This fusion partner may be fused to an antibody-secreting lymphocyte, preferably a B lymphocyte, in order to produce a hybridoma capable of producing homogeneous preparations of antibodies which bind, preferably selectively, to a predetermined immunogen.

The invention further includes an immortalized lymphoid cell line used to produce the fusion partner. These lymphoid cells can be any of a number of differentiating or differentiated lymphoid cells, preferably cells which are capable of producing immunoglobulin. In a preferred embodiment, the lymphoid cells are plasmacytoma cells.

The invention includes a hybridoma, preferably a same-species hybridoma, produced by fusing the fusion partner to an antibody-secreting lymphocyte. In a preferred embodiment, a plasmacytoma-derived fusion partner is fused to a B lymphocyte.

The invention further includes several types of transgenic animals used to produce the lymphoid cell line. In a preferred embodiment, the lymphoid cells are derived from one or more protocols that result in at least one transgene, preferably a double transgene, as described in more detail below.

The invention also includes MAbs produced from the hybridomas. These MAbs specifically bind to a predetermined immunogen and/or may be used in a wide variety of protocols in which MAbs are desirable or useful.

Finally, the invention includes various diagnostic, detection and analytical kits using one or more of the products and/or methods described herein.

As used herein, animal refers to any non-human mammal, including but not limited to rabbits, mice, goats, sheep, guinea pigs, pigs and cows. In a preferred embodiment of the invention, the mammal is a rabbit.

As used herein, expression cassette refers to a sequence of DNA having at least one gene and the sequences necessary for the gene to be expressed in a pre-selected host cell. For example, the gene may be an oncogene, such as myc and/or abl. The sequences necessary for expression include, but are not limited to, a transcription initiation region (including the wild-type sequences for replication), one or more promoters, one or more inducers, one or more enhancers, one or more restriction sites (e.g., a polylinker), and a poly(A) addition signal. The expression cassette may also include one or more selectable markers, such as a drug resistance gene, or a screening marker, such as an HGPRT gene.

As used herein, culture medium or tissue culture refers to a medium that supports the growth of cells. Preparation of culture media is well known by those skilled in the art. Typical ingredients include, but are not limited to, a carbon source, a source of inorganic ammonia (or ammonium ion), a source of phosphate, one or more hormones or growth regulators, one or more vitamins, one or more salts, one or more amino acids, and optionally, other nutrient sources (e.g., glucose or whole serum). Specific examples of culture media in accordance with the invention are described in more detail below. The pH of the culture medium is between 4.5 and 8.5 and the cells are incubated at about 37° C.

In a preferred embodiment of the invention, the fusion partner may be derived from cells obtained from at least one transgenic mammal, preferably a mammal carrying two or more transgenes. Progeny of these mammals develop lymphoid tumors, such as plasmacytomas, which may be harvested and developed into a good fusion partner. Fusing these plasmacytoma-derived fusion partners with spleen cells of immunized mammals results in stable hybridomas that secrete antibodies specific for the immunogen. The hybridomas can be cloned, propagated in culture or in immunodeficient mice such as nude mice, and frozen without change in their ability to secrete specific monoclonal antibodies.

Producing the lymphoid tumor begins with selecting the desired exogenous gene and the sequences necessary for expression of that gene. One skilled in the art knows that cancerous growth or tumors produced by certain oncogenes stimulate the production of a class of lymphoid cells, such as B lineage cells, that have various intermediate and mature phenotypes. Any lymphoid cell that is capable of producing immunoglobulin may be used in accordance with the invention. In a preferred embodiment of the invention, the lymphoid cells are terminally differentiated B lymphocytes. These lymphoid cells are plasmacytomas, cells that are typically identified by a characteristic staining pattern with Wright-Giemsa stain and by chromosomal rearrangements of immunoglobulin. V-(D) and J gene rearrangements are detectable by using a Southern blot analysis.

In accordance with the invention, the plasmacytomas develop in response to the expression of an oncogene or oncogene sequence. More than 20 oncogenes have now been isolated, any of which may be used in accordance with the invention. The preferred oncogenes are myc and abl, which, for convenience, will be cited below as representatives of the class of oncogenes.

It is well known in the art how to isolate and/or obtain an oncogene, and it is equally well known how to construct an expression vector or cassette having an oncogene capable of expression in a suitable cell type. For example, it is known in the art to express a myc gene by using an immunoglobulin heavy chain enhancer, such as the murine system described in Adams, et al., *Nature*, 318:533–38 (1985), incorporated herein by reference. Such a system results in the early and strong expression of the myc gene.

In accordance with the invention, as will be explained below, it may be desirable to induce expression of the oncogene more slowly and/or with less strength. In accordance with a preferred embodiment of the invention, the myc gene may be expressed under the control of an immunoglobulin light chain enhancer (Eκ); and the abl gene may be expressed under the control of an immunoglobulin heavy chain enhancer (Eμ). When these transgenes are introduced into the germ line of a mammal, preferably a rabbit, expression of the transgene may result in tumor growth. An activated oncogene sequence, as the term is used herein, means an oncogene which, when incorporated into the genome of the animal, increases the probability of the development of neoplasms (particularly malignant tumors) in the animal. As noted above, plasmacytomas form as a result of the tumor growth, and, in accordance with one aspect of this invention, these plasmacytomas may be isolated from transgenic mammals.

In general, the invention features a transgenic non-human eukaryotic animal (preferably a rabbit) for the production of the lymphoid cells. Any method for producing the transgenic cells and/or animals may be used. For example, U.S. Pat. 5,087,571 discloses a method for producing a transgenic animal having an activated oncogene. Generally, the transgenic animal has germ cells and somatic cells that contain at least two gene sequences, preferably oncogene sequences, introduced into the animal or an ancestor of the animal. Typically, the oncogene expression cassette is introduced into the mammal at an embryonic stage, preferably the one-cell or fertilized oocyte state, and generally not later than about the eight-cell state.

DNA can be introduced into embryonic stem (ES) cells by transfection, retroviral infection, or electroporation. The most important advantage for gene transfer into animals is that cells carrying the transgene can be selected for before being injected into a blastocyst. For example, ES cells were infected with retroviral vectors, or transfected with plasmids, carrying the neo gene. This gene confers resistance to the antibiotic G418. Only ES cells that have taken up the neo gene grow in medium containing G418, and these G418-resistant cells were introduced into mouse blastocysts. Not only did the resulting animals have neo integrated into their genomes, as shown by Southern blotting, but also the gene was transmitted to the offspring, and cell lines from the F2 generation were G418-resistant. Because ES cells can be manipulated in vitro before injection into the embryo, geneticists can use homologous recombination to produce transgenic animals with mutations, specific genes or to replace a mutant gene with the normal equivalent.

A preferred technique for transferring a cloned gene into an embryo includes microinjecting the cloned genes into fertilized eggs, which contain two pronuclei, one from the sperm (male), and one from the egg (female). These cells ultimately form the nucleus of the one-celled embryo. A few hundred copies of the foreign DNA in about 2 picoliters of solution may be microinjected directly into one of the two pronuclei; the injected embryos are then transferred to the oviduct of a foster mother, and upon subsequent implantation in the uterus, many develop to term. The percentage of eggs that survive the manipulation and develop to term varies, but it is usually between 10 and 30 percent. Of the survivors, the number that have the foreign DNA integrated into their chromosomes is between a few percent and 40 percent. The introduced DNA appears to integrate randomly without preference for a particular chromosomal location, usually in a tandem array of many copies at a single locus. Animals that carry the foreign gene are referred to as transgenic, and the foreign DNA is termed a transgene.

There are several protocols for introducing an oncogene into an animal embryo so as to be chromosomally incorporated in an activated state. One method is to transfect the embryo with the gene as it occurs naturally, then selecting the transgenic animals in which the gene has integrated into the chromosome at a locus which results in activation.

Other activation methods involve modifying the oncogene or its control sequences prior to introduction into the embryo. One such method is to microinject the embryo with an already translocated oncogene. Other methods are to use an oncogene whose transcription is under the control of a synthetic host or viral activating promoter, or enhancer, or to use an oncogene activated by one or more base pair substitutions, deletions, or additions.

In accordance with an embodiment of the invention, the source of the lymphoid-derived fusion partner involves producing a transgenic animal having a first transgene, obtaining fertilized ova from the transgenic animal, then microinjecting (or otherwise inserting) the ova with a second gene. Progeny of this parent can then be screened for having both genes incorporated in the genome.

Another exemplary method includes a transgenic animal having a first transgene and a separate transgenic animal having a second transgene. Mating the first transgenic animal with the second will produce progeny which are double transgenic, i.e., having both the first transgene and the second transgene incorporated in the genome.

Yet, another exemplary method includes microinjecting (or otherwise inserting) a first gene and a second gene into the fertilized ova of an animal and selecting offspring that are transgenic for both genes.

It will be recognized that the gene of interest may be introduced in combination with other cells. For example, it may be desirable to introduce hematopoietic stem cells carrying the transgene in conjunction with embryonic yolk sac, fetal liver, thymus, spleen, or lymph node tissue, fetal or adult bone marrow tissue, pancreatic tissue, appendix tissue, tonsil tissue and the like.

In a preferred embodiment, the chromosome of the transgenic animal includes an endogenous coding sequence (most preferably the c-myc gene, hereinafter the myc gene, and the v-abl gene, hereinafter the abl gene), which is substantially the same as the oncogene sequence, and transcription of the oncogene sequence is under the control of a promoter/enhancer sequence different from the promoter/enhancer sequence controlling transcription of the endogenous coding sequence. The oncogene sequence can also be under the control of a synthetic promoter/enhancer sequence. In some cases, the promoter sequence controlling transcription of the oncogene sequence may be inducible.

One skilled in the art will recognize that progeny carrying the transgene may be identified by Southern blot analysis, by polymerase chain reaction (PCR), and/or by Northern blot analysis.

Once the transgenic animals have been produced and identified, the animals, or their progeny, may be allowed to grow until tumors resulting from the expression of the oncogene(s) are produced. One skilled in the art recognizes that aberrant eating patterns, loss of appetite, lethargy, aberrant growth patterns, and weight loss are external indicators that tumors are developing within the transgenic animal.

Animals having tumor growth may then be used to harvest various differentiated cells, such as lymphoid cells, monocytes, macrophages, B-cells, T-cells, neutrophils, erythrocytes, eosinophils, platelets, and the like. For example, the animal may be sacrificed, and differentiated cells populating the peripheral blood organs, spleen, pancreas, lymph nodes, tonsils, etc., blood, bone marrow, or other tissue(s) may be cultured. In accordance with the present invention, the preferred cells are lymphoid cells, typically plasmacytoma cells.

These lymphoid cells may be frozen and stored, or they may be used as the source of the fusion partner. As used herein, fusion partner refers to cells, typically immortalized cells, that have been altered to exhibit a selectable characteristic once the fusion partner has been used to produce a hybridoma. One skilled in the art will recognize and be capable of choosing any one of several selectable traits. As shown in more detail in the examples, a preferred embodiment of the invention involves irradiating the harvested plasmacytoma cells and culturing the irradiated cells in the presence of 8-azaguanine, a protocol which is known to produce and select HGPRT$^-$ mutants (hypoxanthine guanosine phosphoribosyl transferase). These mutant cells, if not fused into a hybridoma, die when cultured in HAT medium, i.e., these cells exhibit a selectable trait. As used herein, a fusion partner is a lymphoid-derived cell that exhibits a selectable trait and is suitable for fusion with another suitable cell, resulting in a hybridoma. An HGPRT$^-$ plasmacytoma cell is the preferred fusion partner.

A suitable fusion partner may then be fused to a lymphocyte, preferably a B lymphocyte, in order to produce a hybridoma. In a preferred embodiment, the hybridoma is a rabbit-rabbit hybridoma. Typically, spleen cells from hyperimmunized mammals, preferably rabbits, are cultured with the fusion partner under conditions which allow the cells to fuse. When HAT is added to the culture medium, non-fused fusion partner cells will die, thus allowing hybridomas to be isolated. More specific detail of this protocol is shown in the examples.

As is well known in the art, hyperimmunizing the mammal with a preselected immunogen ultimately results in a hybridoma that produces monoclonal antibodies that specifically bind to the immunogen (or antigen). In order to enhance particular subsets of T- and/or B-cells, the mammalian host may be immunized with an antigen of interest to expand the population of T-cells and B-cells that specifically bind to the particular antigen. The mammalian host may be subject to extra immunizations to further enhance the desired population. In this manner, B-cells may be produced which are specific for the antigen, and may be used as splenocytes, lymph node lymphocytes, or other peripheral blood lymphocytes or lymphocytes of other tissue for fusion with a fusion partner according to the invention. More specific detail of an exemplary protocol is shown in the examples.

Various products and reagents used in accordance with the invention may be included in a diagnostic, detection, analytical or experimental test kit. Components of the kit may include analytically detectable immunological reagents capable of detecting the presence of antigen. For example, the kit may contain a carrier or compartment to receive in close confinement therein, means for holding a specimen containing a suspected antigen, a solid support having affixed thereto a monoclonal antibody as described herein and capable of binding to an antigen and an antigen-antibody complex detecting means. The latter can be immunofluorescence means or colorimetric means as is known in the art.

The animals of the invention can also be used as a source of cells for cell culture. Cells from the animals may advantageously exhibit desirable properties of both normal and transferred cultured cells; i.e., they will be normal or nearly normal morphologically and physiologically but can, like cells such as NIH 3T3 cells, be cultured for long, and perhaps indefinite, periods of time. Further, where the promoter sequence controlling transcriptions of the oncogenic sequence is inducible, cell growth increases and other culture characteristics can be controlled by adding or eliminating the inducing factor.

Tissues of transgenic rabbits may be analyzed for the presence of the activated oncogenes, either by directly analyzing DNA or RNA, or by assaying the tissue for the protein expressed by the gene. Cells of tissues carrying the gene can be cultured using standard tissue culture techniques.

EXAMPLE 1

Establishing an Immortalized Plasmacytoma Cell Line from Transgenic Rabbits

We used the transgene (Tg) technology to generate rabbits with plasmacytomas from which we could develop a plasmacytoma cell line. Two rabbits transgenic for two different oncogenes, c-myc and v-abl, were mated and yielded offspring that developed plasmacytomas. One family of Tg rabbits that carried the myc oncogene linked to the light-chain enhancer (EK-myc) and a second family of Tg rabbits carried v-abl linked to the heavy chain enhancer (Eμ-abl). We mated EK-myc Tg rabbits with the Eμ-abl Tg rabbits and screened the offspring by Southern blot analysis for the presence of both transgenes. Several offspring that carried both EK-myc and Eμ-abl transgenes became ill between the ages of 8 and 19 months. When these rabbits were sacrificed, tumors had developed in various locations. Histologic analysis of these tumors revealed that the rabbits had developed immunoblastic lymphoma or early plasmacytoma.

We also used the Tg technology to generate rabbits with plasmacytomas by microinjecting zygotes from EK-myc rabbits with the Eμ-abl Tg. The injected embryos were then implanted in the oviduct of the rabbit and live offspring were delivered. One offspring, 240E1-1, carried both the EK-myc and Eμ-abl Tg and became ill at approximately ten months of age. When this rabbit was sacrificed, tumors had developed in various locations. Histologic analysis of these tumors revealed that the rabbit had developed immunoblastic lymphoma or early plasmacytoma.

To obtain rabbit plasmacytoma cell lines, cells were teased from the tumorous tissues and placed in culture in medium with 15% FCS. Stable cell lines were obtained from five of the six rabbits with plasmacytoma (300F1-2, 0022-3, 20337-7, 20337-8, 240E1-1). These cell lines all synthesized and secreted immunoglobulins.

EXAMPLE 2

Rabbit C-myc Gene

The rabbit c-myc gene was cloned from the rabbit recombinant phage library X314-6 as previously described (Knight et al., *J. Immunol.*, 134:1245–1250) using as probe, a 5.5 Kb EcoRI fragment containing the v-myc gene (Vennstrom et al., *J. Virol.*, 39:625–631, 1981). Positive clones were plaque purified and one, clone 14, was restriction mapped. The 5'-3' orientation of the clone was determined using appropriate v-myc probes and a synthetic DNA oligomer encoding 33 base pairs from a relatively conserved DNA sequence around the human and mouse c-myc TATAAT box (Bernard et al., EMBOJ., 1983, 2:2375–2383).

EXAMPLE 3

Rabbit Kappa Chain Enhancer (EK-myc) DNA Construct

The EK region of rabbit DNA was cloned from the J-C$_k$l region of the 4 k chain locus: The EK1 fragment, a 1.1 kb PstI fragment and the proposed EK2 fragment, a 0.4 kb Bgl II fragment (Emorine et al., 1983, Nature 304:447) were cloned 5' of c-myc into pUC18. The EK-myc construct was cleaved from the plasmid DNA as a 7.5 kb Bam HI/Hind III fragment.

EXAMPLE 4

Transgenic Rabbits

Adult female rabbits were obtained from Scientific Small Animals (Chicago, Ill.). Rabbit zygote donors were injected subcutaneously with 50 IU of pregnant mare gonadotropin (Sigma, St. Louis, Mo.) on day four and immediately after mating, and injected intravenously with 150 IU of chorionic gonadotropin (HCG) (Sigma). Single cell zygotes were flushed from the oviducts 19 hours later. In some experiments, the pronuclei were injected, according to Hammer et al., i Nature, 315:680–683, 1985) with the 7.5 kb Bam HI/Hind III DNA fragment (1 μg/ml) containing both the rabbit c-myc and kappa chain enhancer DNA segments which had been cloned previously into pUC 18. In other experiments, the pronuclei were injected with a 5 kb Eco RI fragment that contained the Eμ-abl construct (see Rosenbaum et al., *The EMBO Journal*, 9:897–905, 1990). The injected zygotes were implanted on day 1 in the oviduct, through the fimbrial end, of a recipient rabbit made pseudopregnant on day 1 by intravenous injection of 150 IU of chorionic gonadotropin (HCG), or by mating with a sterile male.

EXAMPLE 5

Development of EK-myc/Eμ-abl Double Transgenic Rabbits

EK-myc/Eμ-abl double transgenic rabbits were developed by two methods. In the first method, single cell zygotes of the EK-myc transgenic rabbit were collected and microinjected with the Eμ-abl DNA construct. The injected embryos were implanted into the oviduct of the rabbit and live offspring were delivered. Southern blot analysis of DNA from these rabbits showed that one, 240E, was double transgenic, carrying both the $E_\kappa$-myc and the $E_\mu$-abl transgenes. In the second method, rabbits from the Eμ-myc family that carried the EK-myc transgene were mated with rabbits from the Eμ-abl family that carried the EK-abl transgene. Of the progeny, some carried both the EK-myc and Eμ-abl transgene, as determined by Southern analysis.

EXAMPLE 6

Tissue culture

Single cell suspensions for tissue culture were prepared from spleen, mesenteric lymph nodes and bone marrow. Culture medium used throughout was enriched RPMI 1640: RPMI 1640 with the following additions: amino acids, essential amino acids, pyruvate, glutamine, vitamins, HEPES, gentamycin, penicillin and streptomycin, and fungizone. All components are commercially available from Gibco Laboratories, Grand Island N.Y., and were used at the concentrations as suggested by the manufacturer. The medium also contained $5 \times 10^5$ 2-mercaptoethanol.

EXAMPLE 7

Histology Analysis

Cells taken from tissue culture of the plasmacytoma cell lines and paraffin-embedded tissue sections of normal and plasmacytomatous rabbits were stained with Wright-Giemsa (Diff Quick, American Scientific Products, McGaw Park, Ill.) or hematoxylin and eosin, respectively.

Genomic DNA Analysis. Genomic DNA (10 µg), prepared by the method of Blin and Stafford (Nucleic Acid Research, 1976 3:2303–2308) were analyzed using methods described by Southern (J. Mol. Biol., 1975, 98:503–517 (DNA $^{32}$P-labelled probes were prepared as previously described (Knight et al., 1985, supra).

ELISA and Immunofluorescence. Enzyme-linked immunoassay (ELISA) was performed in 96-well microtiter plates (Falcon 3912, Fisher) that were coated overnight with purified goat anti-rabbit L-chain antibody (1 µg/ml) or with the immunogen (2 µg/ml). The following solutions were added, sequentially, for 1–2h at room temperature: first, the supernatants to be tested, then biotinylated goat anti rabbit L-chain or goat anti rabbit µ, γ, or α-chain antibodies (1 µg/ml). This was followed by incubation with avidin-biotin-horseradish peroxidase (HRP) complex (Vectastain ABC Kit, Vectastain, Vector Laboratories, Burlingame, Calif., 94010) and finally with substrate (ABTS) as suggested by the manufacturer. Color development was read at 405 nm in an ELISA plate reader.

EXAMPLE 8

Development of a Rabbit Fusion Partner

To obtain a HAT-sensitive fusion partner, three cell lines were first x-irradiated with 200 Rad and then cultured in the presence of 8-azaguanine to develop an hypoxanthine guanosine phosphoribosyl transferase (HGPRT) mutant cell line that would die when cultured in the presence of hypoxanthanine aminopterin and thymidine (HAT). The concentration of 8-azaguanine was initially 0.2 µg/ml and was slowly increased to 20 µg/ml over a 10-month period. We obtained three 8-azaguanine-resistant clones; 20337-7 after one month and 240E1-1-1 and 240E1-1-2 after 8 months in culture. Cells of those three clones were sensitive to medium containing HAT. In preliminary fusions, we tested whether any of the HAT-sensitive plasmacytoma cell lines could be used as a fusion partner. We fused all three cell lines with spleen cells of a rabbit immunized with the human T-cell line, Jurkat, and we found that one of the three plasmacytoma cell lines, 240E1-1-2, produced hybridomas. We used this cell line for further fusions.

We determined the doubling time of the 240E1-1-2 cells to be 48-72 h (when grown in medium with 15% FCS). By staining with Wright-Giemsa (Diff-Quick, American Scientific Products, Mc Gaw Park, Ill.), the cells had features characteristics of plasma cells, i.e., they are large cells with abundant cytoplasm, and the nuclei frequently contain "lumpy" chromatin. The cells had many vacuoles which indicates that they were proplasmocytes. We assayed for the presence of secreted and intracellular Ig by ELISA and found no Ig heavy or light chain in the supernatant or in the cell lysate of the 240E1-1-2 fusion partner. Thus, this fusion partner unlike the original cell line 240E1-1 neither produces nor secretes Ig. Such a nonsecreting fusion partner is advantageous because it allows us to detect hybridomas by assaying for secreted Ig rather than for secreted antibody with specificity for a given immunogen.

EXAMPLE 9

Fusion of Rabbit Plasmacytoma Cell Line with Rabbit Spleen Cells

Spleen cells of hyperimmunized rabbits and the fusion partner 240E-1-1-2 were fused at a ratio of 2:1 with 50% PEG 4000 (EM Science, Cherry Hill, N.J. 08304) at 37° C. in serum free medium. The cells were plated in 48-well microtiter plates at approximately $2 \times 10^5$ spleen cells per well in medium with 15% FCS. After 72 h, HAT was added. Medium was changed every 5–6 days. Clones usually were observed after 2 weeks. At 3–5 weeks after the fusion, supernatants were tested for the presence of antibody specific for the immunogen either by immunofluorescence or by ELISA. Hybridomas were cloned by limiting dilution in 48-well microtiter plates. As feeder cells we used the fusion partner, 240E1-1-2, $5 \times 10^4$ cells per well. These feeder cells were killed 5–6 days later by the addition of HAT.

EXAMPLE 10

Production of MAb

To further test whether we could obtain stable antibody producing hybridomas, we fused the newly established plasmacytoma line, 240E1-1-2, with spleen cells from rabbits hyper-immunized with three different antigens, the human T cell line, Jurkat, ovalbumin, or mouse serum proteins, including immunoglobulins that were precipitated with 45% saturated $(NH_4)_2SO_4$. We chose these immunogens for the following reasons: Jurkat cells because they are a source of cell surface antigens; ovalbumin because it is a well-known immunogen for rabbit; and mouse Ig because monoclonal isotype-specific antibodies to mouse Ig would be valuable reagents. From all three fusions we obtained hybridomas that secreted MAb specific for the immunogen (Table 1). We used immunofluorescence to test the supernatant of hybridomas obtained from spleen cells of a rabbit immunized with Jurkat cells and found that 10 of 104 hybridomas secreted antibodies that bound to Jurkat cells. We used ELISA to test the supernatant from the hybridomas of the two other fusions and found that 9 hybridomas secreted antibodies specific for ovalbumin and that 43 hybridomas secreted antibodies that recognized antigens of the mouse serum proteins that were used to immunize the rabbit. We also used ELISA to test the supernatant of some of the MAb to mouse serum proteins for their ability to bind to the different mouse Ig isotypes. We found that several of the MAb recognize mouse IgG. We used immunofluorescence to test one MAb that recognizes mouse IgG2 and showed that it binds to IgG2a-expressing B lymphoma cells, A20.

The fusion efficiency for the three fusions performed was between 0.25 and 1.2 in $10^6$ cells, which is comparable to the efficiency generally obtained in mouse-mouse fusions. Of the hybridomas produced, between 9% and 24% secreted MAb that were specific for the immunogens (Table 1). Again, this percentage of hybridomas that secretes specific MAb is comparable to that obtained in mouse-mouse fusions. Using ELISA, we determined the isotype of the antibodies secreted by the hybridomas specific for mouse serum proteins and found that all 43 of them were of the IgG isotype. Of these 43 antibody-secreting clones, we subcloned 7, all of which secreted MAb. The hybridomas could be frozen and thawed without loosing their ability to secrete MAb. These data indicate that the hybridomas are stable and that frequent cloning, which has been necessary for the heterohybridomas, is not needed for the rabbit-rabbit hybridomas.

The concentration of MAb in the supernatant was determined by ELISA. It generated approximately 10 ng/ml, a low concentration that is to be expected if the fusion partner is a proplasmacyte rather than a mature plasma cell. Concentrations of MAb of 1 µg/ml could be obtained in ascites of nude mice. Both the supernatant and the ascites can be used in fluorescence labeling of cell-surface antigens. Most of all of the rabbit MAb are of the IgG isotype, and since rabbit IgG binds protein A and protein G as well as complement, these MAb will also be useful for immunoprecipitation and cytotoxicity assays.

EXAMPLE 11

Frequency and Stability of Hybridomas Obtained in Three Fusions of the Rabbit Fusion Partner with Spleen Cells from Hyperimmunized Rabbits Fusions were performed using conventional methodology: spleen cells ($1.5-3\times10^4$) of hyperimmunized rabbits and the fusion partner 240E1-1-2 were fused at a ratio of 2:1 with 50% PEG 4000 (EM Science, Cherry Hill, N.J. 08304) at 37° C. in serum-free medium. The cells were plated in 48-well microtiter plates, at approximately $2\times10^4$ spleen cells per well, in medium with 15% FCS. After 72 h, RAT was added; the medium was changed every 5–6 days. Clones usually were observed after 2 weeks. At 3–5 weeks after the fusion, supernatant were tested for the presence of antibody specific for the immunogen, either by immunofluorescence with Jurkat cells (by using FITC goat anti-rabbit L-chain antibody as secondary reagent) (fusion 1) or by ELISA (fusions 2 and 3). Hybridomas were cloned by limiting dilution in 48-well microtiter plates. For feeder cells, we used the fusion partner, 240E1-1-2, $5\times10^4$ cells per well. These feeder cells were killed 5–6 days later by the addition of HAT.

| Fusion No: Immunogen | Wells with hybrids/wells plated (%) | Hybrids/$10^6$ cells fused | Hybrids secreting specific Ab/total hybrids tested (%) | Hybrids yielding stable clones/total hybrids cloned (%) |
|---|---|---|---|---|
| 1: Jurkat cells | 200/400 (50) | 0.7 | 10/104 (10) | not done |
| 2: Ovalbumin* | 38/980 (4) | 0.25 | 9/11 (9) | not done |
| 3: Mouse serum proteins | 242/980 (25) | 1.2 | 43/187 (24) | 7/7 (100) |

In the original screening, the supernatant of most wells that contained hybridomas had antibodies that appeared to be specific to the antigen. However, most wells also contained adherent cells, which seemed to support the growth of primary lymphocytes that secreted specific antibody for several weeks. Only after removing the lymphocytes from the layer of adherent cells could we identify true hybridomas. This difficulty likely explained the low number of positive wells in this fusion.

EXAMPLE 12

Immunofluorescence Labeling of Mouse B-Lymphoma Cells A20 with Monoclonal Rabbit Anti-Mouse IgG2 Antibody A20 cells were incubated with the supernatant of a rabbit-rabbit hybridoma (fusion 3) that was shown by ELISA to recognize mouse IgG2a and IgG2b but none of the other mouse Ig isotypes. In control samples, A20 cells were incubated with the supernatant of an IgG-secreting rabbit-rabbit hybridoma that recognizes an irrelevant antigen, i.e., a surface antigen of Jurkat cells (fusion 1). As secondary antibody we used FITC-conjugated goat anti-rabbit L-chain.

EXAMPLE 13

Cloning the HPRT Gene

Animal cells with a homozygous mutation for HPRT were grown in a medium containing hypoxanthine, aminopterin, and thymidine (HAT). Only HPRT⁺ cells can grow in this medium, so the cells that survived and gave rise to colonies were HPRT⁺ revertants. In vitro translation of mRNA from such cells showed that the cells were overexpressing HPRT mRNA. This mRNA may be used to prepare a cDNA library that was differentially screened with radioactively labeled cDNAs prepared from mRNA from the revertant and HPRT⁻ cells. A single clone that did not hybridize with HPRT⁻ cell cDNA and did hybridize with HRPT⁺ revertant cell cDNA was isolated and shown to contain HPRT cDNA by in vitro translation of hybrid-selected mRNA. This animal cDNA was then used to screen a DNA library at low stringency.

EXAMPLE 14

Embryonic Stem Cells (ES cells) Produced from Blastocysts

Rabbits are mated, and 3 days later, blastocysts are isolated and cultured in petri dishes. The cells spread out over the surface of the dish so that the clump of cells forming the inner cell mass, and corresponding to the future embryo, can be removed. The clump of cells is dissociated into single cells using trypsin, a proteolytic enzyme. If ES cells are plated out on a plain culture-dish surface, they will differentiate into a variety of tissues, but if they are grown on a feeder layer of fibroblasts, they will continue to proliferate and can be subcultured repeatedly. A feeder layer, as used herein, refers to a monolayer of cells that has been treated so that the cells can no longer divide. They continue to metabolize, and in so doing "condition" the culture medium so that the cells seeded on top of them survive and grow better. The cells can be microinjected into a blastocyst, where they will become assimilated into the inner cell mass and take part in the formation of many tissues of the chimeric animal. It is usual to use ES cells and recipient blastocysts derived from animals with different phenotypes so that the contribution of the ES cells to the chimeric offspring can be assessed by simply looking for the phenotype.

DEPOSITS

The rabbit plasmacytoma cell line designated 240E1-1, the rabbit fusion partner designated 240E1-1-2 and a hybridoma obtained from fusing the fusion partner, 240E1-1-2, with spleen cells of a hyper-immunized rabbit were deposited with the American Type Culture Collection, 12301 Parklawn Drive, Rockville, Md. 20852, on Apr. 5, 1995 and given respectively, ATCC Accession Nos. CRL-11872, HB-11870, and HB-11871.

OTHER EMBODIMENTS

Although the present invention has been described in terms of particular preferred embodiments, it is not limited to those embodiments. Alternative embodiments, examples, and modifications which would still be encompassed by the invention may be made by those skilled in the art, particularly in light of the foregoing teachings. Therefore, the following claims are intended to cover any alternative embodiments, examples, modifications, or equivalents which may be included within the spirit and scope of the invention as defined by the claims.

We claim:

1. A rabbit fusion partner comprising a transformed rabbit B-lymphocyte which expresses two oncogenes and is capable of fusing with an activated B-lymphocyte wherein said fusion results in a hybridoma that produces immunoglobulins.

2. A rabbit fusion partner of claim 1, which is the rabbit fusion partner of ATCC Accession Number HB-11870.

3. A method of preparing the rabbit fusion partner of claim 1 comprising:
   (a) introducing into a rabbit fertilized egg two expression cassettes each comprising an oncogene;
   (b) transplanting said fertilized egg into a pseudopregnant rabbit;
   (c) allowing said fertilized egg to develop into a rabbit;
   (d) identifying a transgenic rabbit which comprises B-lymphocytes that contain two oncogenes, the expression of which together results in the transformation of said B-lymphocytes;
   (e) isolating said transformed B-lymphocytes from said transgenic rabbit and growing them in culture; and
   (f) selecting said transformed B-lymphocytes by culturing in the presence of a selectable agent, wherein said selecting results in B-lymphocytes that comprise a selectable trait and are useful as a rabbit fusion partner.

4. The method of claim 3, wherein said expression cassette comprises a myc oncogene, an abl oncogene, or a myc oncogene and an abl oncogene.

5. The method of claim 3, wherein said expression cassette further comprises the transcription initiation region for said oncogene and a lymphocyte specific enhancer.

6. The method of claim 3, wherein said selecting results in HGPRT$^-$ cells.

7. A method of preparing the rabbit fusion partner of claim 1 comprising:
   (a) obtaining a first transgenic rabbit comprising a first oncogene that is expressed in rabbit B-lymphocytes, wherein said oncogene by itself does not result in transformation of said rabbit B-lymphocytes, wherein said first rabbit is characterized by germ-line transmission of said first oncogene;
   (b) obtaining a second transgenic rabbit comprising a second oncogene that is expressed in rabbit B-lymphocytes, wherein said oncogene by itself does not result in transformation of said rabbit B-lymphocytes, wherein said second rabbit is characterized by germ-line transmission of said second oncogene;
   (c) mating together said first and said second rabbit to produce an offspring, wherein said offspring comprises said first and said second oncogenes in its germ cells and somatic cells, wherein said first and said second oncogenes are expressed in the B-lymphocytes of said offspring and wherein the expression of said first and said second oncogene together results in B-lymphocytes transformation;
   (d) isolating said transformed B-lymphocytes and growing them in culture; and
   (e) selecting said transformed B-lymphocytes by selecting in the presence of a selectable agent, wherein said culturing results in B-lymphocytes that comprise a selectable trait and are useful as a rabbit fusion partner.

8. The method of claim 7, wherein said first oncogene is a myc oncogene and said second oncogene is an abl oncogene.

9. The method of claim 7, wherein said first or second oncogene comprises the wild-type transcription initiation region for said oncogene and a lymphocyte specific enhancer.

10. The method of claim 7, wherein said selecting results in HGPRT$^-$ cells.

11. A method of preparing the rabbit fusion partner of claim 1 comprising:
   (a) introducing into a rabbit fertilized egg an expression cassette containing two oncogenes;
   (b) transplanting said fertilized egg into a pseudopregnant rabbit;
   (c) allowing said fertilized egg to develop into a rabbit;
   (d) identifying a transgenic rabbit which comprises B-lymphocytes that contain said two oncogenes, the expression of which together results in the transformation of said B-lymphocytes;
   (e) isolating said transformed B-lymphocytes from said transgenic rabbit and growing them in culture; and
   (f) selecting said transformed B-lymphocytes by culturing in the presence of a selectable agent, wherein said selecting results in B-lymphocytes that comprise a selectable trait and are useful as a rabbit fusion partner.

12. A rabbit hybridoma cell line that results from the fusion of the rabbit fusion partner of claim 1 and an activated B-lymphocyte.

13. A method of culturing a rabbit fusion partner which comprises growing the cells of the rabbit fusion partner of claim 1 in an enriched culture medium comprising amino acids, essential amino acids, pyruvate and glutamine.

14. A transgenic rabbit whose germ cells and somatic cells comprise at least two oncogenes each operably linked to a transcription initiation region specific for expression in rabbit B-lymphocytes, wherein the expression of said two oncogenes together results in the transformation of said B-lymphocytes.

15. The transgenic rabbit of claim 14, wherein said transgenic rabbit comprises an $E_\kappa$-myc oncogene and an $E_\mu$-abl oncogene.

16. A method of preparing the transgenic rabbit of claim 14 comprising:
   (a) introducing into a rabbit fertilized egg two expression cassettes each comprising an oncogene;
   (b) transplanting said fertilized egg into a pseudopregnant rabbit;
   (c) allowing said fertilized egg to develop into a rabbit;
   (d) identifying a transgenic rabbit which comprises germ cells and somatic cells that contain said two oncogenes, the expression of which together in its B-lymphocytes results in the transformation of said B-lymphocytes.

17. A method of preparing the transgenic rabbit of claim 14 comprising:
   (a) obtaining a first transgenic rabbit comprising a first oncogene that is expressed in rabbit B-lymphocytes, wherein said oncogene by itself does not result in transformation of said rabbit B-lymphocytes, wherein said first rabbit is characterized by germ-line transmission of said first oncogene;
   (b) obtaining a second transgenic rabbit comprising a second oncogene that is expressed in rabbit B-lymphocytes, wherein said oncogene by itself does not result in transformation of said rabbit B-lymphocytes, wherein said second rabbit is characterized by germ-line transmission of said second oncogene;

(c) mating together said first rabbit and said second rabbit to produce an offspring, wherein said offspring comprises said first and said second oncogenes in its germ cells and somatic cells, wherein said first and said second oncogenes are expressed in the B-lymphocytes of said offspring and wherein the expression of said first and said second oncogenes together results in B-lymphocytes transformation.

18. A transgenic rabbit whose germ cells and somatic cells comprise: (1) a transgene comprising a c-myc oncogene operably linked to an immunoglobulin light-chain enhancer; and (2) a transgene comprising a v-abl oncogene operably linked to an immunoglobulin light- or heavy-chain enhancer, wherein said c-myc oncogene and said v-abl oncogene are expressed in the transgenic rabbit's B-lymphocytes and wherein said expression results in the transformation of said B-lymphocytes.

19. A method of preparing the transgenic rabbit of claim 14 comprising:

(a) introducing into a rabbit fertilized egg an expression cassette containing two oncogenes;

(b) transplanting said fertilized egg into a pseudopregnant rabbit;

(c) allowing said fertilized egg to develop into a rabbit; and (d) identifying a transgenic rabbit which comprises germ cells and somatic cells that contain said two oncogenes, the expression of which together in its B-lymphocytes results in the transformation of said B-lymphocytes.

20. A method of producing monoclonal rabbit immunoglobulins comprising fusing the rabbit fusion partner of claim 1 with an activated rabbit B-lymphocyte under fusing and selective conditions which result in a hybridoma that is capable of producing immunoglobulins, and culturing said hybridoma under conditions such that said immunoglobulins are produced.

21. The method of claim 20, wherein said activated rabbit B-lymphocyte is isolated from a rabbit injected with an antigen.

22. A method for producing rabbit immunoglobulins comprising generating transgenic rabbits having somatic cells and germ cells carrying at least two oncogenes, the expression of which together is effective for the development of plasmacytomas; growing said transgenic rabbits until the rabbits develop plasmacytomas; harvesting said plasmacytomas and fusing the cells of said plasmacytoma with B-lymphoid cells to produce a hybridoma, and incubating said hybridoma under conditions in which the hybridoma secretes immunoglobulins.

23. The rabbit hybridoma cell line of claim 12, which is the hybridoma cell line of ATCC Accession Number HB-11871.

24. A method for producing a rabbit hybridoma cell line comprising fusing the rabbit fusion partner of claim 1 with an activated rabbit B-lymphocyte under fusing and selective conditions to obtain a hybridoma that is capable of producing immunoglobulins.

25. The rabbit plasmacytoma cell line of ATCC Accession Number CRL-11872.

* * * * *

UNITED STATES PATENT AND TRADEMARK OFFICE
CERTIFICATE OF CORRECTION

PATENT NO. : 5,675,063
DATED : Oct. 7, 1997
INVENTOR(S) : Katherine L. Knight

It is certified that error appears in the above-identified patent and that said Letters Patent is hereby corrected as shown below:

In Column 3, line 31: "immunodeficient" should read --immuno-deficient--.
In Column 7, line 53: "Kb" should read --kb--.
In Column 7, line 67: "4" should read --b4--.
In Column 8, line 19: "iNature" should read --Nature--.
In Column 8, line 60: "$5 \times 10^5$" should read --$5 \times 10^5 M$--.

IN THE CLAIMS:
In Claim 7, Column 13, line 61: "selecting" should read --culturing--. (2nd occur.)
In Claim 7, Column 13, line 63: "culturing" should read --selecting--.
In Claim 16, Column 14, line 47: "rabbit;" should read --rabbit; and--.

Signed and Sealed this

Third Day of February, 1998

Attest:

BRUCE LEHMAN

Attesting Officer

Commissioner of Patents and Trademarks